(12) United States Patent
McCleary

(10) Patent No.: US 6,964,969 B2
(45) Date of Patent: Nov. 15, 2005

(54) COMPOSITION AND METHOD FOR TREATING IMPAIRED OR DETERIORATING NEUROLOGICAL FUNCTION

(76) Inventor: Edward Larry McCleary, 1795 Foothills Dr. South, Golden, CO (US) 80401

( * ) Notice: Subject to any disclaimer, the term of this patent is extended or adjusted under 35 U.S.C. 154(b) by 35 days.

(21) Appl. No.: 09/837,562

(22) Filed: Apr. 19, 2001

(65) Prior Publication Data

US 2002/0182196 A1 Dec. 5, 2002

(51) Int. Cl.⁷ .................. A01N 43/42; A01N 37/30; A61K 31/44; A61K 31/205
(52) U.S. Cl. ................ 514/283; 514/295; 514/440; 514/554; 514/565; 514/578; 514/579; 514/690; 514/733; 514/738; 514/762; 424/752
(58) Field of Search .................... 514/25, 49, 279, 514/280, 283, 438, 439, 440, 58; 546/290, 301

(56) References Cited

U.S. PATENT DOCUMENTS

| | | | |
|---|---|---|---|
| 4,812,447 A | | 3/1989 | Roberts |
| 5,104,880 A | | 4/1992 | Kozikowski |
| 5,221,668 A | * | 6/1993 | Henningfield et al. ........ 514/23 |
| 5,668,117 A | | 9/1997 | Shapiro |
| 5,716,614 A | | 2/1998 | Katz et al. |
| 6,020,139 A | | 2/2000 | Schwartz et al. |
| 6,063,820 A | | 5/2000 | Cavazza |
| 6,117,872 A | | 9/2000 | Maxwell et al. |

FOREIGN PATENT DOCUMENTS

| | | |
|---|---|---|
| JP | 401221316 A | 9/1989 |
| JP | 410053256 A | 2/1998 |

OTHER PUBLICATIONS

Tarnopolsky MA, Beal MF. Potential for creatine and other therapies targeting cellular energy dysfunction in neurological disorders. Ann Neurol. May 2001; 49(5): 561–74.

Ferrante RJ, et al., Neuroprotective effects of creatine in a transgenic mouse model of Huntington's disease. J Neurosci. Jun. 15, 2000; 20(12):4389–97.

Miller JW et al., Homocysteine, vitamin B6, and vascular disease in AD patients. Neurology. May 28, 2002; 58(10): 1471–5.

Dhitavat, S. et al.,Acety–L–carnitine protects against amyloid–beta neurotoxicity: roles of oxidative buffering and ATP levels. Neurochem Res. Jun. 2002; 27(6):501–5.

Liu J, et al., Memory loss in old rats is associated with brain mitochondrial decay and RNA/DNA oxidation: partial reversal by feeding acetyl–L–carnitine and/or R–alpha–lipoic acid. Proc Natl Acad Sci USA. Feb. 19, 2002; 99(4):2356–61.

Gonzalez–Perez O, et al., Beneficial effects of alpha–lipoic acid plus vitamin E on neurological deficit, reactive gliosis and neural remodeling in the prenumbra of the ischemic rat brain. Neurosci Lett. Mar. 15, 2002: 321(1–2):100–4.

Baskaya MK, et al., Neuroprotective effects of citicholine on brain edema and blood–brain barrier breakdown after traumatic brain injury. J Neurosurg. Mar. 2000; 92(3):448–52.

Rao AM, et al., CDP–choline: neuroprotection in transient forebrain ischemia of gerbils. J Neurosci Res. Dec. 1, 1999; 58(5):697–705.

Claro FT, et al., Bovine brain phosphatidylserine attenuates scopolamine–induced amnesia. Physiol Behav. Oct. 1999; 67(4):51–4.

Chalon S, et al., Dietary fish oil affects monoaminergic neurotransmission and behavior in rats. J Nutr. Dec. 1998; 128(12):2512–9.

Mischoulon D, Fava M., Role of S–adenosyl–L–methionine in the treatment of depression: a review of the evidence. AM J Clin Nutr. Nov. 2002: 76(5):1158S.

Genedanis S, et al., Influence of SAMe on the modifications of brain polyamine levels in an animal model of depression. Neuroreport. Dec. 21, 2001: 12(18):3939–42.

(Continued)

Primary Examiner—James O. Wilson
Assistant Examiner—Traviss C. McIntosh, III
(74) Attorney, Agent, or Firm—Patton Boggs LLP

(57) ABSTRACT

A nutritional supplement composition for normalizing impaired or deteriorating neurological function in humans is composed of: at least one agent which promotes synthesis of ATP and/or creatine phosphate in the body, at least one antioxidant for scavenging free radicals in at least one pathway in the body; at least one agent for normalizing or maintaining membrane function and structure in the body; at least one agent for normalizing or maintaining normal neurotransmitter function in the body; at least one agent for down-regulating cortisol action; and at least one agent for suppressing activation of apoptotic pathways in the body. The composition may further contain one or more of: at least one agent for suppressing inflammation in the body; at least one agent for normalizing or maintaining vascular wall function and structure in the body; at least one agent for normalizing or maintaining function of nerve growth factors and/or neurotropic factors in the body; at least one agent for suppressing toxic metal ionic effects; at least one agent for normalizing or maintaining methyl metabolism in the body; at least one agent for normalizing or maintaining metabolism of insulin and glucose in the body; and at least one agent for up-regulating activity of heat shock proteins in the body. A method for normalizing impaired neurological function in humans modulating nutrient partitioning in a human involves administering the aforementioned composition to the human, preferably on a daily basis, for a therapeutically effective period of time. Preferably, the method further involves having the human follow a stress reduction program, and/or a cognitive retraining program, and/or a dietary program designed to maximize insulin and glucose metabolism.

5 Claims, No Drawings

OTHER PUBLICATIONS

Pavia J, et al., Effect of S-adenosylmethionine on muscarinic receptors in young rats. Life Sci. 1997; 60(11):825–32.

McCarty MF., Prenatal high-dose pyridoxine may prevent hypertension and Syndrome X in-utero by protecting the fetus from excess glucocorticoid activity. Med Hypotheses. May 2000; 54(5):808–13.

Peng Ol, et al., Pycnogenol protects neurons from amyloid–beta peptide induced apoptosis. Brain Res Mol Brain Res. Jul. 15, 2002; 104(1):55–65.

Turkyilmaz C, et al. Magnesium pre-treatment reduces neuronal apoptosis in newborn rats in hypoxia-ischemia. Brain Res. Nov. 15, 2002; 955(1–2):133–7.

Wang MJ et al., Resveratrol inhibits interleukin–6 production in cortical mixed glial cells under hypoxia/hypoglycemia followed by reoxygenation. J Neuroimmunol. Jan. 1, 2001; 112(1–2):28–34.

Yang O et al., Protective effect of magnesium on the endothelial function mediated by endothelium-derived hyperpolarizing factor in coronary arteries during cardioplegic arrest in a porcine model. J Thoracic Cardiovasc Surgery. Aug. 2002; 124(2):361–70.

Murakami S et al., Taurine suppresses development of atherosclerosis in Watanabe heritable hyperlipidemic (WHHL) rabbits. Atherosclerosis. Jul. 2002; 163(1):79–87.

Pan Y et al., Evidence for up-regulation of brain-derived neurotrophic factor MRNA by soy phytosetrogens in the frontal cortex of retired breeder female rats. Neurosci Lett. Feb. 12, 1999; 261(1–2):17–20.

Brown JE et al., Structural dependence of flavonoid interactions with $Cu^{2+}$ ions: implications for their antioxidant properties: Biochem J. Mar. 15, 1998; 330(pt.3):1173–8.

Niculescu, Mihai D. et al., Diet, Methyl Donors and DNA Methylation: Interactions between Dietary Folate, Methionine and Choline. American Society for Nutritional Sciences, Trans-HHS Workshop: Diet, DNA Methylation Processes and Health, 2002, pp. 2333S–2335S.

Ved HS et al., Huperzine A, a potential therapeutic agent for dementia, reduces neural cell death caused by glutamate. Neuroreport. Mar. 3, 1997; 8(4):963–8.

Martinez-Cruz F et al., Melatonin prevents focal rat cerebellum injury as assessed by induction of heat shock protein (HO–1) following subarachnoid injections of lysel blood. Neurosci Lett. Oct. 18, 2002; 331(3):208–10.

Vas, Adam et al., Clinical and non-clinical investigations using positron emission tomography, near infrared spectroscopy and transcranial Doppler methods on the neuroprotective drug vinpocetine: A summary of evidences. Journal of the Neurological Sciences 203–204,2002, pp. 259–262.

* cited by examiner

COMPOSITION AND METHOD FOR TREATING IMPAIRED OR DETERIORATING NEUROLOGICAL FUNCTION

BACKGROUND OF THE INVENTION

This invention relates to compositions and methods for normalizing impaired or deteriorating neurological function in humans. More particularly, this invention relates to compositions and methods which use a holistic approach for normalizing impaired or deteriorating neurological function in humans.

For various reasons, approximately 20–50% of all the populations of global cultures experience varying types and degrees of nervous system deterioration and/or dysfunction.

Impaired or deteriorating neurological functions are manifested by a variety of conditions spanning a spectrum of states of nervous system dysfunction. Non-limiting examples of such conditions include memory deterioration, certain behavioral problems, attention deficit disorder (ADD), attention deficit hyperactivity disorder (ADHD), other inattention and/or hyperactivity syndromes, dementia or cognitive decline of multiple etiologies, various genetic disorders (e.g., Downs Syndrome, Fragile X Syndrome, etc.), central nervous system (CNS) trauma, intoxications (acute and chronic) or poisoning, auto-immune mechanisms, anoxic-ischemic conditions, neurodegenerative disorders, metabolic afflictions of the nervous system, vascular insults, hypertensive encephalopathy, rheological disorders, demyelination, cerebral edema, inflammatory neuronal conditions, learning disabilities, impulsive behavior, specific emotional or mood problems, difficulty functioning under pressure, various Iatrogenic conditions, infections, eleptogenic foci and congenital brain malformations.

Methods and compositions for treating neurological dysfunction are known in the art.

U.S. Pat. No. 6,020,139 to Schwartz et al. is directed to methods for identifying a therapeutic composition or protocol which ameliorates a disease or undesired condition in a subject, wherein the methods rely upon recognition of the existence of and interconnections between eight S-adenosyl-L-methionine (SAM) pathways. The methods involve determining the presence of the disease or condition in a subject; identifying any abnormalities in each of the eight SAM pathways by determining concentrations of metabolites and/or concentrations or activities of enzymes and/or levels of cellular functions, that are participants in or are results of SAM pathways, thereby obtaining a data set of the differences of the concentrations, activities and/or levels from corresponding normal concentrations, activities and/or levels; analyzing the data set in such a way as to determine which of the metabolites, enzymes and/or cellular functions of the SAM pathways is a causative agent of the differences in concentrations, activities or levels; and identifying a therapeutic composition or protocol which acts to restore the pathways toward normality so as to ameliorate the disease or condition. Diseases or conditions which the methods are designed to treat include Alzheimer's disease, Parkinson's disease, and atherosclerosis. The therapeutic composition used in the invention may be composed of a SAM metabolite or an agent that influences the activity of a SAM pathway or a pathway that is modulated by a SAM pathway. The patent lists compounds the presence and levels of which should be measured and/or monitored in various diseases. For example, for Alzheimer's disease, metabolites, enzyme activities and/or cellular functions which should be monitored include one or more methylation levels, SAM, biotin, polyamines, folate, and vitamin $B_2$. For Parkinson's disease, the metabolites or enzyme activities include polyamines, non-specific N-methylase, acetyl-L-carnitine, $Ca^{2+}$/calmodulin-dependent protein kinase II, lysolecithin, sphingomyelin, SAM and vitamin $B_{12}$. For atherosclerosis, the metabolites, enzyme activities, or cellular functions involve methylation levels, polyamines, acetyl-L-carnitine, calmodulin, and essential phospholipids.

U.S. Pat. No. 5,668,117 to Shapiro discloses a method and composition for treating neurological diseases, wherein the composition contains at least one carbonyl trapping agent alone or in combination with a co-agent or medicament. According to the Shapiro patent, the method and composition can be used to treat, e.g., Alzheimer's disease, Parkinson's disease, hereditary motor and sensory neuropathies, age-onset neurological deterioration, multiple sclerosis, diabetic polyneuropathy, Down's Syndrome, olivopontocerebellar atrophy, amyotrophic lateral sclerosis, alcoholic polyneuropathy, and tinnitus (nerve deafness). According to the patent, co-agents which can be used in the treatment of Parkinson's disease include, e.g., carbidopa and levodopa compositions, dopamine agonists, anticholinergic medications, antihistamines, tricyclic antidepressants, serotonin reuptake inhibitor antidepressants, beta blocker agents, selegiline, D-cycloserine, neurotransmission enhancer drugs, peripheral decarboxylase inhibitors other than carbidopa, N-methyl-D-aspartate glutamate receptor antagonists, tacrine, 9-amino-1,2,3,4-tetrahydroacridin-1-ol, lazabemide, tiapride, and antioxidant agents. The patent teaches that co-agents useful in treating Alzheimer's disease include vasodilator or other nootropic direct brain metabolic enhancer drugs (e.g., idebenone, vinpocetine, and the like), neurotransmission enhancer drugs, tiapride, psychotherapeutic drugs, acetylcholinesterase inhibitors (e.g., huperzine A), calcium channel blocker agents, biogenic amines, antirage drugs, minor tranquilizers, angiotensin-converting enzyme inhibitors, agents which may enhance acetylcholine synthesis, storage or release (e.g., phosphatidylcholine), postsynaptic receptor agonists, ganglioside, specific monoamine oxidase-A inhibitors, N-methyl-D-aspartate glutamate receptor antagonists, nonsteroidal anti-inflammatory agents, selegiline, thiamine, anfacine, sulbutiamine, antioxidant agents, specific monoamine oxidase-B inhibitors, linopirdine, D-cycloserine, and serotonergic receptor antagonists. The Shapiro patent also discusses the use of para-aminobenzoic acid, DL-methionine, vitamin E, panthotenic acid, beta-carotene, selenium, vitamin $B_1$ and a tablet containing folic acid, vitamin $B_2$, vitamin $B_6$, biotin, vitamin $B_1$, niacin, Vitamin $B_{12}$ and panthotenic acid, to treat a human suffering from hereditary motor and sensory neuropathy.

U.S. Pat. No. 4,812,447 to Roberts discloses a method for treating nervous system deterioration associated with aging and Alzheimer's disease, involving administering a therapeutically effective amount of dehydroepiandrosterone (DHEA) or its sulfate and, optionally, a potassium channel antagonist. The Roberts patent is further directed to pharmaceutical compositions containing DHEA, alone or in combination with a potassium channel antagonist, e.g., 4-aminopyridine. The patent teaches that DHEA facilitates the growth of nervous system tissue.

U.S. Pat. No. 5,104,880 to Kozikowski discloses the use of huperzine A analogs as acetylcholinesterase inhibitors which may be useful for treating memory and learning disorders such as, e.g., Alzheimer's disease, myasthenia gravis, and other age-related memory impairments.

U.S. Pat. No. 5,716,614 to Katz et al. discloses a pharmaceutical composition for treating diseases relating to severe deterioration of the central nervous system (e.g., dementias, neurodegenerative disorders, neurological diseases, malignant brain tumors, and inborn errors of metabolism), wherein the composition contains a complex of a polycationic carrier (e.g., poly-lysine, poly-arginine, or poly-ornithine) coupled to eicosapentaenoic acid or docosahexaenoic acid moities, a biologically active agent and one or more additional docosahexaenoic acid moieties. The one or more additional docosahexaenoic acid moieties are selected from docosahexaenoic acid-containing phosphatidyl serine, docosahexaenoic acid-containing phosphatidyl ethanolamine, and phosphatidyl carnitine.

Japanese Patent JP401221316A discloses a cerebral circulatory metabolism-improving agent composed of idebenone and vinpocetine.

Japanese Patent JP410053526A discloses a composition for treating, among other things, nervous symptoms caused by Alzheimer's disease, wherein the composition contains a vitamin $B_1$ derivative or its salt and idebenone.

U.S. Pat. No. 6,063,820 to Cavazza is directed to a medical food for diabetics which includes linolenic acid, alkanoyl-L-carnitine, and, optionally, coenzyme A, antioxidants (e.g., lipoic acid, resveratrol, glutathione, selenium, and the like), taurine, pantethine, vitamin A, vitamin E, vitamin $B_1$, vitamin $B_6$, vitamin $B_{12}$, magnesium, calcium, zinc, selenium, chromium, and vanadium. The patent teaches that peripheral neuropathies of the autonomic nervous system may be among the late complications of disease.

U.S. Pat. No. 6,117,872 to Maxwell et al. discloses a composition for enhancing exercise performance by augmenting endogenous nitric oxide production or activity, the composition containing L-arginine, L-lysine, and, optionally, antioxidants (e.g., vitamins A, C and E, cysteine, glutathione), or other factors which may enhance endothelial-derived nitric oxide (EDNO) synthesis or activity, such as folic acid, biopterins, B complex vitamins (specifically, $B_6$ and $B_{12}$), flavonoids (e.g., resveratrol), carotenoids (e.g., lycopene, phytoestrogens), L-carnitine, L-creatine, and L-taurine.

Current sophisticated investigative techniques have facilitated ever greater insight into the subtle abnormalities responsible for the diverse neurological conditions mentioned previously herein. As knowledge of these complex mechanistic pathways of disease has accumulated, many potential sites have become available for possible therapeutic intervention. The basic pathways which either individually or collectively are responsible for neurological deterioration or dysfunction may generally be classified as follows:

1) bioenergetics or the intrinsic ability of individual neurons or neural networks to generate and/or utilize an adequate, continuous supply of readily usable fuel to power the ongoing needs of every individual cell under steady state as well as adverse conditions;
2) nitrogenous and/or oxidative stress;
3) apoptosis;
4) maintenance of cellular and subcellular membrane structure and function, fluidity, permeability characteristics, receptor and channel activity, and signal transducing capability;
5) neurochemistry and neurotransmission;
6) vascular wall integrity and function;
7) neurotransmission;
8) protection of nuclear and mitochondrial DNA;
9) maintenance of neuronal plasticity;
10) inflammation;
11) nerve growth factors;
12) metal ionic effects;
13) aberrant methyl metabolism;
14) cortisol (glucocorticoid) activity;
15) insulin action; and
16) stress protein activity.

Bioenergetics

Cells use energy to make new proteins, to bring nutrients into cells, to expel cellular wastes, to repair damaged DNA, to synthesize neurotransmitters, to conduct electrical nerve impulses, etc.

The basic unit of energy in all cells is the molecule adenosine triphosphate (ATP), which is primarily generated within the cell's mitochondria. Neurons requires a continuous and substantial production of ATP to fulfill ongoing metabolic requirements. ATP is formed by the bonding of three phosphate groups to a molecule of adenosine. The bonds between the phosphate groups are unstable and, when broken, release a tremendous amount of energy for cell events. When one phosphate group is broken off of ATP, adenosine diphosphate (ADP) and a free phosphate group result, and energy is available.

The creation of ATP involves extracting energy from nutrients such as, e.g., carbohydrates, proteins and fats. Nutrients contain an abundant supply of covalent bonds which are a source of potential energy. When these bonds are broken, energy is available to synthesize ATP.

In neurons, the difference between ATP supply and ATP demand is small even under optimal circumstances. Recent evidence posits diminution or reversal of this energy gradient as a primary cause of neurodegeneration, especially under adverse conditions.

ATP does not come ready-made in the foods we eat. Cells must each generate their own ATP from the glucose, fatty acids and amino acids derived from the digestion of the carbohydrates, fats and proteins provided by foods. After digestion/absorption by the stomach/small intestine and processing by the liver, molecules of glucose, fatty acids, and amino acids are transported through the bloodstream to the cells which will convert these nutrient molecules into ATP. Once inside the cell, these fuel molecules are processed through four interlocking ATP-energy production cycles, i.e., glycolysis, the Kreb's cycle, the electron transport chain, and/or creatine phosphate (CP).

Dysfunctional bioenergetics involve abnormalities of substrate supply/metabolism, disturbed passage of high energy electrons along the respiratory chain, and impaired calcium homeostasis. These alterations affect the cellular processing of amyloid precursor protein (APP).

The neuron is limited by its availability of a energy-generating substrate, being required to use primarily either glucose, ketone bodies or lactate. The neuron does not produce or store glucose or ketone bodies and cannot survive for any significant period of time without a substrate, which is absorbed and used directly or indirectly from the bloodstream. Thus, a constant supply of substrate must be present in the blood at all times in amounts sufficient to supply the entire brain and the rest of the body with fuel. Brain cells require a concentration of about 5 mM glucose (or its equivalent) in order to maintain its optimal rate of oxidative phosphorylation to produce ATP. Certain groups of brain cells play a central role in the regulation of glucose and fat metabolism throughout the body.

Nutrients enter cells by passing through the cell membrane. Nutrient delivery frequently relies upon mechanisms outside the cell membranes such as oral intake, absorption, circulatory transport and interstitial flux. Once localized in the vicinity of the cell, membrane-specific processes play a role in nutrient transport sequentially across the blood-brain barrier and then into the interior of the cell and on into various subcellular organelles.

Nutrient transport is made possible by the breakdown of ATP by molecules called ATPases. It has been recognized that $Na^+$ gradients, which are created by $Na^+/K^+$ ATPases, are used by many cells to transport nutrient molecules across cell membranes.

Dysfunctional bioenergetics may also involve disturbed passage of high energy electrons along the respiratory chain.

In addition, dysfunctional bioenergetics involve impaired calcium homeostasis. The regulation of calcium plays a central role in the proper functioning and survival of neurons. Calcium pumps located on cell membranes use ATP to transport calcium ions out of the neuron. Proper activity of the calcium pump is essential in the maintenance of neuronal, mitochondrial, and endoplasmic reticulum (ER) homeostasis. Alterations in pump function modulate enzyme activity within the cell and also play a critical role in triggering the mitochondrial permeability transition which may lead to cell death. Dysfunctional intracellular $Ca^{2+}$ metabolism is believed to contribute to cell death in Alzheimer's disease.

Oxidative Stress

Oxidative stress is a condition in which the production of oxy free radicals outstrips endogenous free radical protective mechanisms. This impairs neuronal metabolism and function via two separate mechanisms: (1) direct free radical damage to important cellular biomolecules including membrane lipids, nucleic acids and functional proteins; and (2) modulation by oxy radicals of critical signal transduction pathways.

Membrane Structure and Function

Neural function is dependent upon around the clock transmission of electrical impulses between cells trillions of times per day in a continuous fashion. This activity relies upon the precise actions of multiple membrane proteins, each suspended in a phospholipid bilayer. The optimal activity of this dynamic membrane microenvironment is critically dependent upon the exact status and chemical composition of the lipid constituents. Lacking the appropriate phospholipid environment, the myriad cell channel proteins, enzymes and receptors would not be able to achieve sustained levels of maximal function without subsequent potentially disastrous consequences.

In addition, oxidative stress and/or abnormal methyl metabolism reduces the fluidity of the membranous lipid bilayer with subsequent adverse effects upon embedded functional proteins.

Neurochemistry/Neurotransmission

Appropriate intercellular cross talk between neurons is requisite for normal neurological function. In fact, this plays a major role in determining neuronal plasticity—the inherent ability of past synaptic activity to modulate and direct such future activity. This occurs by continuously upgrading neurotransmitter flux and remodeling neuronal cell processes. These mechanisms form the basis for the evolution of all complex thought processes. Neurotransmitters constitute the family of chemical compounds secreted by neurons into the narrow extra-cellular clefts which define the boundaries between closely packed neuronal processes. These are numerous, with new candidates being discovered continuously. The main neurotransmitters are acetylcholine (ACH), norepinephrine (NE), gamma-amino-butyric acid (GABA), dopamine (DO), serotonin (S), glutamate (G), and nitric oxide (NO). Alterations in neurotransmitter levels directly contribute to neurological dysfunction in various disorders via altered effects upon membrane signal transduction and intracellular metabolic signaling pathways. ACH levels are low in Alzheimer's Disease (AD), primarily in the area of the basal forebrain and hippocampus (especially the nucleus basalis of Meynert), NE and DO activity are diminished in ADD/ADHD syndromes. DO is abnormal in Parkinson's Disease (PD). Serotonin activity is abnormally low in depressive states. These primary neurotransmitter abnormalities rarely exist alone. Disruption of normal noradrenergic function has also been implicated in AD and schizophrenia. Studies exist documenting the efficacy of cholinergic therapy in ADD/ADHD. Evidence shows that nicotinic activation enhances dopaminergic neurotransmission. There also seems to be duality of effect between different catecholaminergic neurotransmitters. This knowledge is also important because of the relative overlap in certain neurologic diagnostic categories and supports an open-minded treatment approach potentially using various combinations of neurotransmitter modulating interventions.

Elevated glutamate and nitric oxide exposure, accompanied by low ACH levels, play key roles in the development of and symptomatology related to various neurodegenerative processes.

In addition to producing symptoms by changing cell function via modulation of synaptic transmission, alterations in neurotransmitters may also contribute to pathologic disease processes at the cellular level. The role of ACH in AD is one such example. In this circumstance, the neurotransmitter ACH acts as a trophic factor for the neuronal cell body and processes. Upon withdrawal of such neurotrophic modulation abnormal cellular metabolic changes are initiated. One such pathway which may be triggered involves alterations in the normal processing mechanism for APP. Normally with cleavage of APP, soluble neurotrophic remnants are produced. However, exposure to cholinergic withdrawal modifies this process with the subsequent production of an APP remnant of beta-amyloid protein. This process initiates pathways in the neuron, resulting in oxidative stress, maladaptive nutrient partitioning, and subsequent neurodegenerative changes. Therefore, therapeutic treatments which augment cholinergic tone would be expected to ameliorate this pathophysiologic process.

Therapeutic interventions have been used to address certain specific aspects of neurotransmission but have not been components of a comprehensive holistic approach such as presented in the current invention. Examples of previously used individual mono-therapies include: (1) provision of additional substrate for synthesis of various neurotransmitters (e.g., choline, CDP-choline, phosphatidyl choline, dimethylaminoethanol (DMAE), and various amino acids); (2) stimulation of production and secretion of neurotransmitters (e.g., phosphatidyl serine increases DO, NE and ACH; CDP-choline increases DO, ACH and NE; huperzine A increases DO, NE and ACH and vinpocetine increases NE);

(3) inhibition of enzymes used to degrade various neurotransmitter molecules within the region of the synaptic cleft (e.g., huperzine A, an acetylcholinesterase inhibitor); (4) re-uptake inhibitors (e.g., ritalin blocks DA re-uptake); (5) provision of agents that facilitate improved binding at the receptor site (e.g., phosphatidyl serine); (6) direct agonists (e.g., pergolide is a DA agonist); (7) induction of enzymes used to synthesize neurotransmitters (e.g., soy phytoestrogens increase choline-acetyl transferase (CHAT)); and (8) augmentation of neurotransmitter receptor sites (e.g., SAMe increases ACH receptor sites).

Apoptosis

Apoptosis refers to the energy-requiring process of programmed cell death whereupon an individual nerve cell under the appropriate circumstances embarks upon a process equivalent to cellular suicide. Certain of the mechanisms discussed above may initiate these pathways. These include oxidative stress, calcium overload, cellular energy deficiency, trophic factor withdrawal, and abnormal APP processing.

An additional pathophysiologic mechanism of neuronal degeneration involves excessive activation of excitotoxin-induced apoptotic pathways. Glutamate acting at NMDA receptors mediates such a process.

Inflammation

Various conditions of metabolic dysfunction are associated with many of the chronic diseases afflicting westernized societies. These include cellular resistance to the effects of the hormone insulin, increasing abdominal visceral adipose tissue, hypertriglyceridemia, chronic subclinical inflammation, hyperleptinemia, abnormal sympathetic tone, and increased hypothalamic-pituitary-adrenal activity. Intrinsic to the dysmetabolic conditions listed above are sustained elevations of Interleukin-1 (IL-1), Interleukin-6 (IL-6), activation of the complement cascade, hyperfibrinogenemia, elevated C-Reactive Protein (CRP), increased Plasminogen Activator Inhibitor (PAI) levels, hypercoagulability, monocytic and microglial activation, and an increased acute phase response (APR). A direct effect of these factors, especially with regard to the up-regulation of IL-1 and IL-6, is activation of the hypothalamic axis. Increases in ACTH and cortisol are seen in association with decreases in growth hormone and gonadotropins. This change in hypothalamic function is associated with increased extracellular excitatory amino acid (EAA) levels in that region of the brain.

Specific components of the inflammatory cascade are active in the Alzheimer's diseased brain. Cytokines such as Interleukin-1 (IL-1) and Interleukin-6 (IL-6) contribute to maturation of neuritic plaques and neurodegeneration by augmenting the production of beta-Amyloid. Complement components are increased in the Alzheimer's diseased brain and interact with beta-Amyloid to recruit glia. Activated microglia may function as antigen presenting cells as well as sources of cytokines, complement and neurotoxins.

There are two isoforms of the enzyme cyclooxygenase: COX-1 and COX-2. COX-1 is constitutively expressed and COX-2 is inducible. COX-2 is the isoform that mediates inflammation. COX-2 mRNA levels increase in the presence of IL-1. There is evidence that COX-2 mRNA is regulated in neurons by synaptic activity. Dramatic up-regulation of COX-2 mRNA is seen in hippocampal neurons in response to excitotoxic stimuli. The induction of COX-2 mRNA overlaps the onset of apoptosis in hippocampal pyramidal neurons. These findings support the concept that COX-2 is involved in mechanisms of inflammation and neuronal cell death.

The primary substrate for COX-2 is arachidonic acid which is released by the action of phospholipase A2 upon membrane phospholipids. Substances which increase intracellular calcium, such as glutamate and beta-Amyloid, activate phospholipase A2. One of the reactions catalyzed by COX-2 involves generation of PGH-2 and induces production of a free electron which is donated to molecular oxygen to form the superoxide radical. Free radical mediated lipid peroxidation in turn activates COX-2, thus forming a positive feedback loop. This reinforces the role of COX-2 in neurodegeneration.

Vascular Mechanisms

Disease and auto-regulatory dysfunction of the vascular wall contribute to neurological deterioration. Interactions of endothelial cells with various components of flowing blood must also be evaluated as an avenue leading to nerve cell death and/or dysfunction. Mechanistically, this involves limitation in blood flow due to functional as well as structural vascular wall pathology and their interaction with rheologic factors.

The ability of blood vessels to dilate and contract in response to metabolic needs and to retain a smooth, non-adherent, non-occlusive vascular lumen is required for normal brain function. This depends critically upon adequate function of nitric oxide pathways within the endothelial cells and their interactions with platelets and plasma proteins. Additional factors involve blood viscosity and flexibility of the red blood cells which is in part dependent upon the lipid makeup of their cell membrane.

Nerve Growth/Neurotrophic Factors

There is evidence that many of the neurodegenerative changes associated with brain aging may be caused, in part, by a decline in the activity of a class of neurochemicals called "Nerve Growth Factors" (NGF). NGF provide support for the healthy functioning of brain cells. Nerve growth factors such as Brain-Derived Neurotrophic Factor (BDNF) are widely expressed in the brain with highest levels seen in the hippocampus followed closely by the cerebral cortex. Existing data indicate that BDNF modifies the long term survival, differentiation and synaptic activity of the neurons in the hippocampus and cerebral cortex as well as cholinergic neurons in the septal region. In Alzheimer's disease, BDNF mRNA is reduced significantly in the hippocampus and temporal cortex. These data suggest that BDNF is involved in preserving the integrity and function of cholinergic neurons and their target tissues. BDNF deficiency therefore contributes to neurodegeneration. Other agents may act in a trophic fashion by utilizing the phosphatidyl-inositol-3 kinase ($PI_3K$) signaling pathway, e.g., insulin and insulin-like growth factor-1 (IGF1).

Metal Ion Effects

When certain metallic ions interact with specific neuronal constituents, they are able to impair the actions of numerous functional proteins in addition to producing damage to the delicate membrane lipids. Metals bind to sulfhydryl (SH), OH, $NH_2$, and Cl groups in proteins, enzymes, co-enzymes, and cell membranes. Such metal binding interferes with cellular processes, changing membrane charge and permeability and the antigenicity of autologous structures.

Metals in ionic form reach cell membranes attached to circulating blood proteins, particularly the water-soluble component of lipoproteins. Here, the affinity is strongest for SH-containing molecules such as methionine, cysteine, and glutathione. This feature allows ionic metals to exchange freely between lipoprotein and the macromolecules of ligands of cell membranes, including red blood cells. The hemoglobin of red blood cells is particularly rich in SH groups, which further explains how ionic metals reach the various cell membranes via blood.

By binding to cell membranes, metals change the membrane charge, which may result in changed membrane permeability, dysfunction and cell death. Metals also bind to mitochondria, thereby impairing cellular respiration.

Free radical formation, cell membrane disturbance, and enzyme inhibition can each mediate the toxic effects of metals.

Iron is a potent pro-oxidant which has been linked with dopaminergic neuronal cell death in PD. Lead interacts with the NMDA receptor to produce adverse effects. Neuronal aluminum concentration has been linked to Alzheimer's disease.

Methyl Metabolism

Factors which compromise methyl metabolism (i.e., the transfer of methyl groups between biologically active compounds) play key roles in the development of various neurological diseases. Methylation deficiency is also important in the basic process of aging. This is especially true regarding methylation of DNA and homocysteine. If DNA is not kept properly methylated, the appropriate regulation of gene expression is impaired, both in the cell nucleus and the mitochondria. This induces profound alterations in the smooth functioning of the cellular metabolic machinery and also impairs mitochondrial energy production, which as discussed previously herein, is a critical process, especially in neurons. Elevated homocysteine levels have been associated with the development of Alzheimer's disease and are a well known risk factor for vascular disease and stroke.

Dysfunctional methylation also initiates oxidative stress which activates the nuclear transcription factor NFKB. When NFKB enters the nucleus, it binds to specific DNA binding sites and initiates intracellular inflammatory pathways which act in a cascading fashion to further disrupt cellular homeostasis.

Proper methylation has many benefits.

Methylation is essential in the production of melatonin, a hormone secreted by the pineal gland and having anti-cortisolic action.

Adequate methyl processing faciliates the breakdown and elimination of histamine, which, in the central nervous system, is a neurotransmitter with excitotoxic actions. The breakdown and elimination of histamine produces anti-inflammatory effects in the brain.

Methylation of certain proteins is essential for proper functioning. Myelin basic protein (MBP) is a component of the myelin sheath which surrounds each nerve cell and is vital for normal neuronal function. MBP is dependent upon methylation to adequately carry out its function in the myelin sheath.

Normal neurotransmitter function is critically dependent upon activity of protein channels and receptors in the cell membrane. The function of such protein channels and receptors is determined by the fluidity of the membrane phospholipid bilayer in which the functional proteins are embedded. Adequate methylation processes ensure appropriate membrane fluidity. This not only affects neurotransmission which is specific to nerve cells, but also modulates transport of sodium and potassium ions in and out of each cell.

Further interactions between methyl pathways and functional proteins involve maintenance and repair processes which decline with age. The decline of these processes plays a role in the development of neurodegenerative processes in the central nervous system, e.g., Alzheimer's disease.

Cortisol (Glucocorticoid) Activity

Intrinsic to various dysmetabolic conditions are sustained elevations of Interleukin-1 (IL-1), Interleukin-6 (IL-6), activation of the complement cascade, hyperfibrinogenemia, elevated C-Reactive Protein (CRP), hypercoagulability, monocytic and microglial activation, and increased APR. A direct effect of these factors, especially with regard to the up-regulation of IL-1 and IL-6, is activation of the hypothalamic-pituitary-adrenal axis (HPAA). This change in hypothalamic function is associated with increased extracellular excitatory amino acid (EAA) levels in that region of the brain.

Activation of the HPAA produces sustained elevations of glucocorticoid (cortisol) activity which has been shown to have detrimental effects upon neurons. The brain region most affected is the hippocampal formation which is intimately involved with memory and cognition. Located within the hippocampus is the nucleus basalis of Meynert (NDM). This is the central processing site for acetyl choline (ACH). When ACH levels fall, memory loss and aberrant cognition ensue. These are the hallmark symptoms of AD. The prolonged exposure of the hippocampal neurons to cortisol produces not only functional changes but also morphologic alterations such as rounding and loss of neuronal processes. This diminished surface contact among neurons alters neurotransmission and may lead to the production of beta-amyloid.

Beta-secretase is an enzyme in the brain which cleaves beta-amyloid from its precursor protein APP. It is sensitive to inhibition by soy phytoestrogenic isoflavones. Genistein also stimulates the enzyme CHAT which synthesizes ACH. Additional actions of this group include the induction of synthesis of Brain-Derived Neurotrophic Factor (BDNF). This is important because withdrawal of trophic influences initiates apoptotic pathways, and low BDNF levels are seen in Alzheimer's disease.

Insulin Action

The hormone insulin is considered functionally to act as a neurotrophic agent in the central nervous system. It has anabolic properties which increase neuronal protein synthesis. Neuronal insulin receptors act to increase glucose metabolism in nerve cells. Resistance to this action of insulin in the brain has been produced by excess glucocorticoid tone as well as by other systemic metabolic abnormalities which decrease insulin sensitivity. This produces a cellular metabolic deprivation effect. Mechanisms which augment insulin action in neurons facilitate the contribution of glucose to the cellular production of ATP and, in so doing, improve neuronal bioenergetics.

Increased intraneuronal glucose availability acts to maintain glutathione in its reduced state and also provides a substrate for ACH, glutamates, and other neurotransmitter synthesis.

Insulin resistance is associated with elevated EAA within the hypothalamus and subsequent increases in glucocorticoid activity. Agents which up-regulate glutamate transport or act as insulin sensitizing agents benefit the brain of those suffering from Alzheimer's disease.

Augmentation of insulin sensitivity also enhances constitutive nitric oxide pathways. Adequate function of nitric oxide pathways is critical to the ability of blood vessels to dilate and contract in response to metabolic needs and to retain a smooth, non-adherent, non-occlusive vascular lumen required for normal brain function.

In addition, interventions which improve insulin-sensitivity are, by their very nature, anti-inflammatory.

Heat Shock/Stress Protein Activity

Heat shock proteins or stress proteins are families of essential proteins found in almost all prokaryotic and eukaryotic cells. Heat shock proteins are essential for normal cell functions and are expressed both constitutively and in increased amounts when cells are stressed in a variety of ways.

It has been found that mild metabolic stress can increase the resistance of neurons to subsequent more severe insults. An increase in levels of stress proteins such as heat shock protein-70 (HSP-70) and glucose-regulated protein-78 (GRP-78) are believed to contribute to the neuroprotective effects of mild stress.

For various reasons, approximately 20%–50% of the global population experience varying types and degrees of nervous system deterioration and/or dysfunction. This produces a tremendous personal, social and financial burden on society. It is desirable to provide a means for preventing, lessening, modifying or reversing this situation.

Although therapeutic interventions have been used to address individual aspects of impaired neurological function, it is desirable to provide a comprehensive holistic approach for the treatment of neurological abnormalities. When complex, interrelated disease pathways are involved in an abnormal physiologic condition, a single agent will not provide significant beneficial action. Multiple sites of intervention are mandatory. In abnormal neurological conditions, as discussed above, the broad general areas requiring intervention include inflammation, APP processing, cortisol homeostasis, hypothalamic activation, insulin action, oxidative stress, excitotoxic mechanisms, and altered calcium physiology. Thus, what is required to make progress in neurological protection and treatment is a program using multiple simultaneous avenues of intervention designed to generate maximal synergistic activity.

U.S. Pat. No. 5,668,117 to Shapiro is directed to therapeutic compositions and methods for treating mammals suffering from a neurological disease characterized by covalent bond crosslinking between the nerve cells, other cellular structures and their intracellular and extracellular components, with disease induced carbonyl-containing aliphatic or aromatic hydrocarbons present in mammals. Examples of such diseases include Alzheimer's disease and age-related neuron degeneration. The therapeutic composition for treating Alzheimer's disease may contain at least one carbonyl trapping agent to compete with and covalently bind to the disease-induced carbonyl-containing aliphatic or aromatic hydrocarbons; a vasodilator or other nootropic direct brain metabolic enhancer co-agent (e.g., idebenone, vinpocetine, phosphatidylserine, etc.); a neurotransmission co-agent; ifenprodil; tiapride; a psychotherapeutic co-agent; an acetylcholinesterase inhibitor (e.g., huperzine A); a calcium channel blocker co-agent; a biogenic amine; an anti-RAGE co-agent; a benzodiazepine tranquilizer; an angiotensin-converting enzyme inhibitor; a co-agent which enhances acetylcholine synthesis, storage or release (e.g., phosphatidylcholine); an acetylcholine postsynaptic receptor agonist; ganglioside $GM_1$; mixed cow brain gangliosides; a specific monoamine oxidase-A inhibitor; an N-methyl-D-aspartate glutamate receptor antagonist; a non-steroidal anti-inflammatory co-agent; selegiline; thiamine; sulbutiamine; anfacine; an anti-oxidant co-agent; a specific monoamine oxidase-B inhibitor; linopirdine; D-cycloserine; a serotonergic receptor antagonist; vitamins; co-agents which facilitate glutathione biological activity, hormones; and free-radical trapping compounds.

The use of nicotinamide adenine dinucleotide in treating such neurological diseases as Parkinson's disease and Alzheimer's disease is discussed in SOUTH, JAMES, NADH the body and mind energizer [online], [retrieved on Apr. 4, 2001]. Retrieved from the Internet: <UR http://www.smart-drugs.net/ias-NADH.htmL>.

Accordingly, a primary object of this invention is to provide a composition and a method which use a holistic approach to normalize impaired neurological function in humans.

This and other objects are achieved in the present invention.

SUMMARY OF THE INVENTION

The present invention provides a composition and method for treating impaired neurological function or deteriorating neurological function in the body of a human.

A first aspect of the present invention is directed to a nutritional supplement composition for normalizing impaired or deteriorating neurological function in the body of a human having impaired or deteriorating neurological function, wherein the composition contains effective amounts of:

(A) at least one agent which promotes synthesis of adenosine triphosphate (ATP) and/or creatine phosphate in the body;

(B) at least one antioxidant for scavenging free radicals in at least one pathway in the body;

(C) at least one agent for normalizing or maintaining membrane function and structure in the body;

(D) at least one agent for normalizing or maintaining normal neurotransmitter function in the body;

(E) at least one agent for down-regulating cortisol action; and (F) at least one agent for suppressing activation of apoptotic pathways in the body; with possible inclusion of one or more of the following:

(G) at least one agent for suppressing inflammation in the body, (H) at least one agent for normalizing or maintaining vascular wall function and structure in the body;

(I) at least one agent for normalizing or maintaining function of nerve growth factors and/or neurotropic factors in the body;

(J) at least one agent for suppressing toxic metal ionic effects;

(K) at least one agent for normalizing or maintaining methyl metabolism in the body;

(L) at least one agent for normalizing or maintaining metabolism of insulin and glucose in the body; and (M) at least one agent for up-regulating activity of heat shock proteins in the body.

A second aspect of the present invention is directed to a method for normalizing impaired or deteriorating neurological function in the body of a human having impaired neurological function, wherein the method involves orally administering to the human for a therapeutically effective period of time the composition of this invention. The composition is preferably administered on a daily basis.

The nutritional supplement composition of this invention was developed systematically in a holistic fashion by identifying the multiple, interrelated pathophysiologic pathways and mechanisms which interact to varying degrees and culminate in specific clinical manifestations of neurological system disease, dysfunction or deterioration. Once the important disease-producing pathways were established, each was individually analyzed, and the loci of specific control mechanisms, modulating factors and rate-limiting steps were identified. At each of these loci, therapeutic interventions were developed that were designed to normalize the individual micrometabolic aberrations. Using this model, a therapeutic paradigm was developed to maximize interventional efficacy by capitalizing on the intrinsic synergy of such an approach.

Thus, the present invention not only improves symptomalogy but actually functions at various sites to produce metabolic and physiologic changes which alter, modulate and improve or reverse the basic abnormalities responsible for the development of various neurological diseases.

Furthermore, since the various aberrant pathways are integrated and interrelated to varying degrees and, therefore, functionally augment each other's pathologic effects, the present invention's holistic approach is able to block this negative synergism.

As stated above, the present invention uses a multimodal neurofacilitatory approach. Along with the above-identified approach using nutritional supplements, the present invention also preferably involves a dietary approach designed to optimize glucose and insulin metabolism, a stress reduction program designed to down-regulate the hypothalamic-pituitary-adrenal axis (HPAA) and lower cortisol levels, and/or a cognitive retraining program.

Thus, the present invention produces beneficial effects at many sites in various dysfunctional pathways. The invention prevents, lessens, or reverses the attendant neurological symptomalogy and, at the same time, ameliorates their causative mechanisms.

DETAILED DESCRIPTION OF THE INVENTION

As stated above, the present invention is directed to a composition and a method for normalizing impaired neurological function in the body of a human. The composition is composed of effective amounts of various nutritional supplements which provide a holistic approach to normalizing impaired neurological function. The method of the invention involves the administration of an effective amount of the composition preferably in conjunction with a stress reduction program and/or a cognitive retraining program and/or a dietary plan designed to maximize insulin and glucose metabolism.

As used herein, the term "impaired neurological function" refers to deteriorating or defective neurological function.

With respect to the amounts of the individual components of the composition of this invention, the term "effective amount" means that amount of the component which, when used in combination with the other components in the composition, will provide the composition with the capability of normalizing impaired neurological function in humans.

As stated above, neurons need continuous, substantial production of ATP to fulfill ongoing metabolic requirements.

The most rapid way to generate ATP is through phosphorylation of adenosine diphosphate (ADP) by creatine phosphate.

Thus, the composition of this invention includes an effective amount of (A) at least one agent which promotes synthesis of ATP and/or creatine phosphate in the body.

Preferably, component (A) of the composition of this invention is selected from one or more of the following compounds: Co-enzyme Q10, idebenone, taurine, acetyl L-Carnitine (ALC), nicotinamide adenine dinucleotide (NADH), phosphatidyl serine, B-vitamins, vinpocetine, oral creatine (which can be provided as creatine monohydrate), cytidine-5'-diphosphocholine, ribose and alpha lipoic acid (ALA).

As mentioned above, dysfunctional bioenergetics involve abnormalities of substrate supply/metabolism, disturbed passage of high energy electrons along the respiratory chain and impaired calcium homeostasis.

Co-enzyme Q10 facilitates high energy electron transfer along the respiratory chain with resultant augmentation of ATP synthesis. Idebenone, a co-enzyme Q10 analogue, may be used in a similar fashion.

Taurine supplementation is desirable in the present invention because of taurine's ability to beneficially modulate calcium balance in neurons.

ALC, a compound with excellent central nervous system penetration, helps fatty acids across the mitochondrial membrane where the fatty acids may be used as an energy source. ALC enhances brain energy production by improving mitochondrial function and is also a beneficial modulator of mitochondrial DNA synthesis—a process which is closely linked with cellular energy metabolism.

NADH is a nutritional substance which facilitates ATP production in neurons.

Phosphatidyl serine acts as a mitochondrial protectant. It is located within the inner mitochondrial membrane and is intimately involved in mitochondrial function.

B vitamins are cofactors in numerous neuronal bioenergetic pathways, and pharmacologic supplementation ameliorates or normalizes neurologic dysfunction due to poor nutritional intake or excessive neuronal energy demands.

Vinpocetine is a derivative of vincamine which is an extract of the periwinkle. It is a powerful metabolic enhancer by beneficially modulating Krebs Cycle activity and thus stepping up central nervous system (CNS) ATP production.

Oral creatine augments neuronal levels of high energy phosphate compounds in vivo. Oral creatine is preferably provided as creatine monohydrate.

Cytidine-5'-diphosphocholine (CDP-choline) is a donor of choline which is used in the synthesis of both phosphatidyl choline, an important brain phospholipid, and the important neurotransmitter acetyl choline (ACH). Oral administration of CDP-choline also reactivates brain mitochondrial ATPases and the Na/K ATPases.

Ribose is a pentose ring carbohydrate which is well absorbed and may become a rate-limiting substrate in the synthesis of 5-phosphoribose-1-pyrophosphate (PRPP) under conditions of excessive energy demands. Hence, ribose supplementation facilitates cellular energy production and mitochondrial bioenergetics.

Supplementation with the cofactor ALA augments energy production.

In a preferred embodiment, component (A) comprises a combination of oral creatine and ALA. Preferably, in such embodiment, the creatine:ALA ratio ranges from about 1:30 to about 2500:1, more preferably from about 1:10 to about 1000:1.

The composition of this invention also contains (B) at least one antioxidant for scavenging free radicals in at least one pathway in the body. Preferably, component (B) is one or more antioxidants selected from the following: idebenone, co-enzyme Q10, vitamin E, ALA, vitamin C, carnosine, tocotrienols, flavonoids, ALC, vinpocetine, selenium, lycopene, creatine, certain amino acids (e.g., arginine, taurine, and cysteine), NADH, resveratrol, ginkgo biloba, oligomeric proanthocyanidins, and phenolic antioxidants.

Although a single antioxidant can scavenge free radicals in the body, antioxidative therapy is most effective when multiple antioxidants are used as a network, where the antioxidants continuously interact with one another in a beneficial fashion to maximally suppress oxidative events in many interrelated pathways. Thus, in a preferred embodiment, component (B) is composed of two or more, preferably all, of the antioxidants listed above.

In a particularly preferred embodiment, component (B) is composed of a combination of taurine and cysteine. Preferably, the taurine:cysteine ratio in such embodiment ranges from about 1:20 to about 60:1, more preferably from about 1:20 to about 15:1.

The composition of this invention further contains (C) at least one agent for normalizing or maintaining membrane function and structure in the body.

Preferred agents for component (C) include one or more of the following: gamma linolenic acid (GLA); highly polyunsaturated long chain fatty acids such as docosahexanoic acid (DHA), phosphatidyl serine (PS), phosphatidyl choline (PC), phosphatidyl ethanolamine (PE), and phosphatidyl inositol (PI); CDP-choline; methyl donors; S-adenosyl methionine, and antioxidants (e.g., one or more of the antioxidants which can be used as component (B) of the composition of this invention) and sphingosine.

Essential fatty acid deficiency mimics many of the symptoms of ADD/ADHD. This is consistent with an association between alterations in membrane function and the development of specific neurological disease.

CDP-choline plays a major role in the synthesis of phosphatidyl choline, thus protecting the integrity of neuronal cell membranes, membrane function and repair mechanisms.

Oxidative stress reduces the fluidity of the membranous lipid bilayer with subsequent adverse effects upon embedded functional proteins. Antioxidant therapy as well as supplementation with methyl donors or S-adenosyl methionine (SAMe) can mitigate these adverse effects.

Preferably, component (C) comprises a combination of DHA and phosphatidyl serine (PS), preferably at a DHA:PS ratio of from about 1000:1 to about 1:100, more preferably from about 50:1 to about 1:10.

The composition of this invention further comprises (D) at least one agent for normalizing or maintaining normal neurotransmitter function in the body.

Such an agent for component (D) may comprise one or more of the following: (1) an agent for synthesis of various neurotransmitters, non-limiting examples of such substrate including choline, CDP-choline, phosphatidyl choline, dimethyl minoethanol (DMAE), and various amino acids; (2) an agent for stimulation of production and secretion of neurotransmitters, non-limiting examples of such substrate being phosphatidyl serine (which increases DO, NE and ACH), CDP-choline (which increases DO, ACH and NE), and vinpocetine (which increases NE); (3) an agent for inhibition of enzymes used to degrade various neurotransmitter molecules within the region of the synaptic cleft, a non-limiting example of such substrate being Huperzine A, an acetylcholinesterase inhibitor, (4) a re-uptake inhibitor (e.g., ritalin, which blocks DA re-uptake); (5) an agent that facilitates improved binding at the receptor site (e.g., phosphatidyl serine); (6) a direct agonist (e.g., pergolide, which is a DA agonist); (7) an agent for induction of enzymes used to synthesize neurotransmitters (e.g., soy phytoestrogens, which increase choline-acetyl transferase (CHA); and (8) an agent for augmentation of neurotransmitter receptor sites (e.g., SAMe, which increases ACH receptor sites).

In a preferred embodiment, component (D) comprises a combination of DMAE and huperzine A. Preferably, the DMAE:huperzine A ratio in such embodiment ranges from about 2000:1 to about 1:15, more preferably from about 2000:1 to about 67:1.

Component (E) of the composition of this invention is composed of at least one agent for down-regulating activity of cortisol in the body. Preferably, component (E) comprises one or more agents selected from the group consisting of phosphatidyl serine, DHEA, melatonin, and pyridoxine.

The composition of this invention also contains (F) at least one agent for suppressing activation of apoptotic pathways in the body.

Preferred agents for use as component (F) include one or more of the following: vinpocetine, huperzine A, magnesium, calcium channel blockers, resveratrol, pycnogenol, and lycopene.

Vinpocetine, huperzine A and magnesium each counteract the action of glutamate at NMDA receptors. Glutamate action at NMDA receptors mediates the activation of excitotoxin-induced apoptotic pathways, which in turn can lead to neuronal degeneration.

Activation of NMDA receptors produces elevations in intracellular calcium concentration. Thus, calcium channel blockers and resveratrol (which also decreases calcium influx) can serve a protective function against such elevations in calcium concentration.

Activation of NMDA receptors also increases nitrergic tone within neurons. Pydiogenol counteracts this effect. Any such induced elevation of intraneuronal nitric oxide contributes to the generation of peroxynitrite which is very sensitive to quenching by the action of lycopene.

In a preferred embodiment, component (F) comprises a combination of huperzine A and vinpocetine. In a particularly preferred embodiment, component (F) comprises a combination of huperzine A and vinpocetine in a huperzine A;vinpocetine ratio of from about 1:2 to about 1:200.

Component (G) of the composition of this invention comprises at least one agent for suppressing inflammation in the body.

Preferably, component (G) comprises one or more agents selected from the following: COX-2 inhibitor (e.g., resveratrol), CDP-choline, phosphatidyl serine, DHEA, melatonin, pyridoxine, magnesium, GLA, long chain omega 3 fatty acids, insulin-sensitizing agent (e.g., chromium), antioxidants and vitamin C.

As discussed previously herein, COX-2 mediates inflammation in the body. Thus, COX-2 inhibition forms another therapeutic avenue. Resveratrol is a natural compound with significant COX-2 inhibitory activity.

COX-2 mRNA levels increase in the presence of Interleukin-1 (IL-1). CDP-choline usage lowers IL-1 levels.

Inflammatory processes have been associated with increases in glucocorticoid activity caused by elevated EAA levels within the hypothalamus. Phosphatidyl serine, DHEA, melatonin, vitamin C, and pharmacologic doses of pyridoxine each have anti-cortisolic effects.

Interventions which improve insulin sensitivity are by their very nature anti-inflammatory. Weight loss and specific dietary changes also act in a synergistic fashion to decrease inflammatory mediators.

The mineral magnesium has been shown to have beneficial actions involving the stabilization of neuronal membranes and is able to down-regulate excitatory neurotransmission by direct negative allosteric effects upon the NMDA receptor.

GLA and long chain omega 3 fatty acids play a key role in down-regulating the inflammatory cascade.

Antioxidants are effective at impairing the induction of Nuclear Factor Kappa Beta (NFKB), a potent inflammatory transcription factor.

Component (H) of the composition of this invention comprises at least one agent for normalizing or maintaining vascular wall function and structure in the body.

Preferably, component (H) comprises at least one agent selected from the group consisting of magnesium, L-arginine, L-taurine, antioxidants, insulin-sensitivity enhancers, long chain polyunsaturated fatty acids, vinpocetine, choline, betaine, vitamin $B_6$, vitamin $B_{12}$, folic acid, and supplemental potassium.

Supplemental magnesium has vasodilatory effects. L-arginine drives the constitutive nitric oxide pathway which further dilates blood vessels and helps to maintain proper endothelial function. Antioxidants play a key role in this regard by preventing inactivation of nitric oxide. Augmentation of insulin sensitivity further enhances these nitric oxide pathways. Supplementation with long chain polyunsaturated fatty acids or vinpocetine enhances red blood cell deformability will subsequent improvements in nutrient delivery through the smallest caliber vascular channels. Elevated serum homocysteine levels are toxic to endothelial cells and impair endothelial cell function.

Augmentation of methylation pathways by the use of nutritional supplements such as creatine, choline, betaine, vitamin $B_6$, vitamin $B_{12}$, folic acid, dehydroepiandrosterone (DHEA), phosphatidyl serine, S-adenosyl methionine (SAMe), zinc and selenium enhances vascular function and nutrient delivery to the central nervous system. Methyl donors lower homocysteine levels.

Component (I) of the composition of this invention comprises at least one agent for normalizing or maintaining function of nerve growth factors and/or neurotropic factors in the body.

Preferably, component (I) comprises one or more agents selected from the group consisting of estrogenic compounds (e.g., estradiol and soy phytoestrogens), idebenone, and propentofylline.

Estrogenic compounds increase the expression of the anti-apoptotic protein Bcl-XL in hippocampal neurons. This effect represents estrogen transcriptional regulation since a putative estrogen response element has been identified in the bcl-x gene. Enhancement of Bcl-XL is associated with a reduction in measures of beta-Amyloid-induced apoptosis and inhibition of both caspase-mediated proteolysis and neurotoxicity. Both estradiol and soy phytoestrogens have been shown to significantly increase mRNA levels of BDNF which has antiapoptic activity. Hence, soy phytoestrogens are able to act as estrogenic agonists in the brain without possessing the unwanted side effects of enhancing the risk of breast and uterine cancer. Idebenone and propentofylline both enhance the synthesis of nerve growth factors. Agents tending to augment cholinergic tone have also been shown to have a similar neuronal trophic effect. The hormone insulin is also considered functionally to act as a neurotrophic agent. It has anabolic properties which increase neuronal protein synthesis. Neuronal insulin receptors have been described which act to increase glucose metabolism in nerve cells. Resistance to this action of insulin in the brain has been produced by excess glucocorticoid tone as well as by other systemic metabolic abnormalities which decrease insulin sensitivity and subsequently diminish its trophic action.

Component (J) of the composition of this invention comprises at least one agent for suppressing toxic metal ionic effects caused by interaction between toxic metal ions and neuronal constituents in the body. As used herein, the term "toxic metal ionic effects" refers to metal ion activities which impair cellular processes in the body. Examples of toxic metal ions include iron, lead and aluminum.

Preferably, component a) comprises one or more agents selected from the group consisting of desferroximine, alpha-lipoic acid (ALA), zinc, silicon and polyphenolic antioxidants.

Desferroximine and ALA function as chelators for toxic metals in the central nervous system. Zinc, while not acting as a true metal chelator, acts to reverse the adverse effects caused by the interaction of lead with the NMDA receptor. Silicon reduces neuronal aluminum accumulation which may be related to the development of Alzheimer's disease. Polyphenolic antioxidants achieve iron detoxification.

The composition of this invention further comprises (K) at least one agent for normalizing or maintaining methyl metabolism in the body.

Preferably, component (K) comprises one or more agents selected from the group consisting of dehydroepiandrosterone (DHEA), phosphatidyl serine, S-adenosyl methionine (SAMe), choline, folic acid, vitamin $B_6$, vitamin $B_{12}$, betaine, zinc, selenium, and creatine.

Zinc also plays a key role because of the zinc finger appendages on one of the most important enzymes in DNA regulation, specifically, DNA methyl transferase.

Vitamin $B_6$, DHEA and phosphatidyl serine exhibit cortisol-ameliorating effects. The stress reduction element of the present invention also produces cortisol-ameliorating effects.

SAMe is a high energy methyl donor. SAMe's methyl groups make possible the production of carnitine and creatine (both of which play key roles in cellular bioenergetics); the neuronutrient, acetyl-L-carnitine; the stress hormone and neurotransmitter, adrenaline; the neuronutrient and chief membrane phospholipid, phosphatidyl choline; and the DNA bases, methyladenine and methylcytosine.

SAMe also plays a major role in the synthesis of acetyl choline (ACH), which is one of the most important neurotransmitters, especially involving memory, attention, cognition and executive functioning. The provision of exogenous SAMe has been beneficial as a stand alone agent in ADD/ADHD trials, and use in treatment for depression has been described.

Selenium has been shown to raise SAMe levels when supplemented in its selenomethionine form.

The composition of this invention also contains (L) at least one agent for normalizing or maintaining metabolism of insulin and glucose in the body. Component (L) is designed to improve systemic sensitivity to the insulin. Mechanisms which augment insulin action at the nerve cell membrane facilitate the contribution of glucose to the cellular production of ATP and, in so doing, improve neuronal bioenergetics.

Preferably, component (L) comprises (a) one or more agents which down-regulate glutamatergic tone (e.g., huperzine A or magnesium supplementation), and/or (b) one or more insulin-sensitizing agents (e.g., chromium).

Component (M) of the composition of this invention comprises at least one agent for up-regulating activity of heat shock proteins in the body.

The composition of this invention preferably includes a pharmaceutically acceptable carrier. As used herein, the term "pharmaceutically acceptable carrier" is meant to include one or more pharmaceutically suitable, inactive excipients, carriers, diluents, adjuvants, and lubricants. Non-limiting examples of inactive excipients, carriers, diluents, lubricants, and adjuvants which can be used in the composition of the present invention include: cellulose, substituted cellulose, calcium carbonate, dicalcium phosphate, starches, lactose, modified food starches, dextrose, calcium sulfate, magnesium carbonate, magnesium stearate, stearic acid, glycerin, vegetable oils, polysorbates, lecithin, silicium dioxide, food glaze, talc, croscarmellose sodium, povidone, water and gelatin. Additional inactive excipients, carriers, diluents, lubricants and adjuvants which may be used with the active-ingredient composition of this invention are disclosed in the Handbook of Food Additives (CRC Press), which is incorporated by reference herein in relevant part.

The pharmaceutically acceptable carrier can be present in any conventional amount used in an orally administered composition.

Set forth in the table is a preferred embodiment of the orally administered composition (excluding inactive ingredients) of this invention. The amounts recited in the table represent preferred and more preferred daily dosages of the ingredients listed.

| Ingredient | Effective Range | Preferred Range |
|---|---|---|
| Thiamine | 1 mg–200 mg | 10 mg–100 mg |
| Riboflavin | 1 mg–1000 mg | 10 mg–500 mg |
| Niacin | 1 mg–3000 mg | 25 mg–750 mg |
| Carnosine | 1 mg–1000 mg | 20 mg–500 mg |
| Pyridoxine | 1 mg–300 mg | 25 mg–200 mg |
| Folic Acid | 50 mcg–10 mg | 200 mcg–2 mg |
| B 12 | 25 mcg–2 mg | 100 mcg–1 mg |
| Biotin | 10 mcg–10 mg | 50 mcg–2 mg |
| Pantothenic Acid | 1 mg–500 mg | 10 mg–200 mg |
| Vitamin C | 10 mg–2000 mg | 50 mg–1000 mg |
| Vitamin E | 1 IU–2000 IU | 10 IU–1000 IU |
| Magnesium (chelated) | 10 mg–2000 mg | 100 mg–1200 mg |
| Zinc (chelated) | 2 mg–50 mg | 5 mg –25 mg |
| Selenium (as selenomethionine) | 10 mcg–600 mg | 20 mcg–300 mcg |
| Chromium | 25 mcg–2000 mcg | 50 mcg–1200 mcg |
| Potassium | 5 mg–150 mg | 20 mg–100 mg |
| OPC | 2 mg–150 mg | 10 mg–75 mg |
| Cysteine | 100 mg–2000 mg | 200 mg–1000 mg |
| Taurine | 100 mg–6000 mg | 500 mg–3000 mg |
| Acetyl L-Carnitine | 10 mg–3000 mg | 25 mg–2000 mg |
| Creatine Monohydrate | 100 mg–25 g | 500 mg–5 g |
| DMAE | 20 mg–2000 mg | 50 mg–200 mg |
| Choline | 20 mg–10 g | 50 mg–2 g |
| Inositol | 20 mg–10 g | 50 mg–2 g |
| Phosphatidyl Serine | 5 mg–1000 mg | 50 mg–400 mg |
| Phosphatidyl Choline | 5 mg–2000 mg | 50 mg–1000 mg |
| Phosphatidyl Ethanolamine | 5 mg–1000 mg | 50 mg–400 mg |
| Phosphatidyl Inositol | 5 mg–2000 mg | 50 mg–1000 mg |
| DHA (docosahexanoic acid) | 10 mg–5000 mg | 25 mg–2000 mg |
| Vinpocetine | 1 mg–30 mg | 2 mg–20 mg |
| Huperzine A | 10 mcg–500 mcg | 50 mcg–300 mcg |
| Coenzyme Q10 | 1 mg–1000 mg | 5 mg–400 mg |
| L-Arginine | 100 mg–9000 mg | 200 mg–8000 mg |
| Idebenone | 100 mg–400 mg | 270 mg–360 mg |
| GLA | 5 mg–500 mg | 50 mg–200 mg |
| Silicon | 2 mg–40 mg | 5 mg–20 mg |
| Alpha Lipoic Acid | 10 mg–1000 mg | 50 mg–600 mg |
| Resveratrol | 10 mg–300 mg | 50 mg–200 mg |
| Soy Isoflavones | 10 mg–200 mg | 50 mg–100 mg |
| CDP-Choline | 25 mg–1000 mg | 100 mg–400 mg |
| NADH | 1 mg–20 mg | 5 mg–10 mg |
| DHEA | 5 mg–200 mg | 25 mg–100 mg |
| Melatonin | .5 mg–15 mg | 1 mg–5 mg |
| Ribose | 500 mg–10 g | 1 g–5 g |
| Lycopene | 1 mg–30 mg | 5 mg–15 mg |
| Betaine | 100 mg–3000 mg | 500 mg–1500 mg |
| Gingko Biloba | 10 mg–1000 mg | 25 mg–600 mg |

The composition presented in the table above is preferably in the form of an orally administered composition, e.g., powder, chewable wafer, tablet, regular or compressed capsule, etc., wherein the amounts listed are divided into two portions which in combination constitute a single "serving" or "unit dose" of the composition. Each serving is preferably with 8 ounces of water.

The method of this invention involves the steps of administering (preferably daily) for a therapeutically effective period of time to a human having impaired or deteriorating neurological function an effective amount of the composition of this invention. The composition is administered orally or parenterally preferably orally.

As used herein with respect to the amount of the composition used in the method of this invention, the term "effective amount" means an amount sufficient to normalize impaired or deteriorating neurological function in a human. Preferably, the active-ingredient composition (not including inactive ingredients) of this invention is administered in a per serving (e.g., daily) dosage of at least about 1 gram, more preferably from about 1 gram to about 40 grams, most preferably from about 0.25 grams to about 30 grams. When inactive ingredients are present in the composition, the inactive ingredients of the composition can be present in any conventional amount used in orally or parenterally administered compositions.

The term "therapeutically effective period of time" with respect to the administration of the composition in the method of this invention means that period of time sufficient to normalize impaired or deteriorating neurological function in the human. Preferably, the composition of this invention is administered on a daily basis for a period of at least three weeks, more preferably at least six weeks.

As stated above, oral administration is accomplished by ingesting the composition, preferably with water. The orally administered composition of this invention can be in any conventional form including, e.g., capsules (regular or compressed), tablets, chewable wafers, elixirs, powders, granules, suspensions in water or non-aqueous media, sachets, etc.. Powder, tablet, and chewable wafer forms are most preferred.

Alternatively, the composition can be administered parenterally.

As stated above, the method of the present invention may include the human following a stress reduction program which is designed to down-regulate the hypothalamic-pituitary-adrenal axis and lower cortisol levels. The stress reduction program is intended to augment the effects of the nutritional supplement aspect and, if included, the cognitive retraining aspect (discussed below), of the invention. The stress reduction program varies from individual to individual but would involve partaking in activities which reduce stress. Non-limiting examples include, e.g., relaxation, getting a massage, acupuncture, psychotherapy, meditation, taking a sedative, and the like.

The method of the present invention also preferably includes having the human follow a cognitive retraining program. Such a program would act to retrain the brain by inducing changes in neuronal metabolism, neurochemistry/neurotransmission, restructuring of neural circuitry and dendritic/axonal arborization patterns, and increasing synaptosomal surface area and intercellular contacts.

The present invention may further include a nutritional or dietary plan which is designed to improve systemic sensitivity to insulin and to maximize insulin and glucose metabolism. Non-limiting examples include restriction of calories, and/or restriction of refined carbohydrates, and/or restriction of saturated fat, and/or restriction of trans-fat.

Much knowledge has been accumulated regarding etiologic processes as well as possible treatment and/or preventative modalities involving functional brain deterioration. Because of the multiple coexistent pathways of injury which may play a role in any particular scenario, it is no surprise that many prior therapies have been less than effective. However, due to increased understanding of the integrated nature of neuronal pathways of disease, the utility of analyzing all individual pathologic mechanisms at each potentially therapeutic site with the goal of developing a therapy that addresses the entire network of abnormalities involved clearly represents a quantum advance. It is by this analytic process that a truly unique and comprehensive therapeutic paradigm is provided in the present invention.

What is claimed is:

1. A composition for treating impaired neurological function or treating deteriorating neurological function in the body of a human, or for promoting neurological health or maintaining neurological health in the body of a human, said composition comprising effective amounts of:
    (A) at least one agent which promotes synthesis of ATP and/or creatine phosphate in the body, wherein said (A) agent is selected from the group consisting of creatine monohydrate, alpha lipoic acid, and trimethylglycine;
    (B) at least one antioxidant for scavenging free radicals in at least one pathway in the body, wherein said (B) agent is selected from the group consisting of taurine, ginko bioba, lycopene, acetyl L-carnitine, vinpocetine, alpha lipoic acid, coenzyme Q10, and resveratrol;
    (C) at least one agent for treating or maintaining membrane function and structure in the body, wherein said (C) agent is selected from the group consisting of inositol and choline;
    (D) at least one agent for treating or maintaining normal neurotransmitter function in the body, wherein said (D) agent is selected from the group consisting of DMAE and choline;
    (E) at least one agent for down-regulating cortisol action, said (E) agent comprising pyrodoxine; and,
    (F) at least one agent for suppressing activation of apoptotic pathways in the body, said (F) agent comprising huperzine;
    wherein said (A), (B), (C), (D), (E), and (F) agents are present in said composition in effective amounts for treating impaired neurological function or treating deteriorating neurological function in the body of a human, or for promoting neurological health or maintaining neurological health in the body of a human.

2. A composition according to claim 1, wherein said agent (A) further comprises B-vitamins.

3. A composition according to claim 1, wherein said agent (B) further comprises ALA.

4. A composition as in claim 1, said composition comprising effective amounts of alpha lipoic acid, acetyl L-carnitine, choline, pyridoxine, and huperzine.

5. A composition as in claim 4, said composition further comprising effective amounts of creatine monohydrate, inositol, taurine, trimethylglycine, vinpocetine, coenzyme Q 10, resveratrol, and ginko biloba.

* * * * *